United States Patent
Zelechonok

(10) Patent No.: US 10,371,672 B1
(45) Date of Patent: Aug. 6, 2019

(54) INTEGRATED CHROMATOGRAPHY COLUMN INJECTOR DETECTOR DEVICE

(71) Applicant: Yury Zelechonok, Northbrook, IL (US)

(72) Inventor: Yury Zelechonok, Northbrook, IL (US)

( * ) Notice: Subject to any disclaimer, the term of this patent is extended or adjusted under 35 U.S.C. 154(b) by 403 days.

(21) Appl. No.: 15/099,990

(22) Filed: Apr. 15, 2016

Related U.S. Application Data

(60) Provisional application No. 62/147,697, filed on Apr. 15, 2015.

(51) Int. Cl.
*G01N 30/22* (2006.01)
*G01N 30/74* (2006.01)

(52) U.S. Cl.
CPC ............ *G01N 30/22* (2013.01); *G01N 30/74* (2013.01)

(58) Field of Classification Search
CPC .. G01N 30/22; G01N 30/74; G01N 2030/201; G01N 2030/743; G01N 2030/746
See application file for complete search history.

(56) References Cited

U.S. PATENT DOCUMENTS

| | | | |
|---|---|---|---|
| 3,475,950 A * | 11/1969 | Ferrin | G01N 30/20 73/23.41 |
| 4,522,715 A | 6/1985 | Walters | |
| 5,778,681 A | 7/1998 | Li et al. | |
| 5,983,710 A | 11/1999 | Uhen et al. | |
| 8,173,070 B2 | 5/2012 | Gerhardt et al. | |
| 2009/0321338 A1 * | 12/2009 | Natarajan | B01D 15/1864 210/198.3 |
| 2011/0025047 A1 * | 2/2011 | Zelechonok | F16L 37/138 285/212 |
| 2012/0184722 A1 * | 7/2012 | Samper | G01N 21/05 534/10 |

* cited by examiner

*Primary Examiner* — Xin Y Zhong
(74) *Attorney, Agent, or Firm* — John C. Shepard

(57) ABSTRACT

A chromatography device includes a unitary body that mounts and connects together as an integrated unit a chromatography column, an sample injector and a detector cell. The device components are arranged generally along X-Y-Z space axes. This arrangement allows hydraulic connection of all the components without additional tubing, fittings, or threaded ports. It also allows an integrated chromatography device to be produced inexpensively by machining or injection molding. The disclosed arrangement allows a user to have convenient access to the components for replacement or service. In addition, the disclosed construction enhances chromatography efficiency, reduces pressure, improves temperature control, and eliminates cross-contamination.

18 Claims, 4 Drawing Sheets

INTEGRATED CHROMATOGRAPHY COLUMN INJECTOR DETECTOR DEVICE

CROSS-REFERENCE TO RELATED APPLICATIONS

This application claims the benefit of Provisional Patent Application Ser. No. 62/147,697, filed Apr. 15, 2015.

BACKGROUND OF THE INVENTION

Technical Field

The present invention relates to an integrated chromatography device and, more particularly, to a simple device that can be used to combine a chromatography injector, a detector and a column into a single device.

Background Art

High pressure liquid chromatography ("HPLC") systems usually include a high pressure pump, an autosampler or some other sample introduction device, a chromatography column, and a detector.

Typically, the sample is a solution of analytes in an appropriate solvent. The required amount of the sample is injected into the chromatography liquid stream generated by the high pressure pump and is separated into individual components in the column. The separated sample components are measured individually by the detector.

The typical configuration of the chromatography equipment comprises of a pump, an injector unit, a column holding unit, and detector. Each unit can be completely separate devices with own mechanical, electrical, and electronic components. In another style, the units can share some common elements like an enclosure or a power source. Each unit is typically connected with high pressure liquid lines or tubing to provide continuous flow of liquid serially from the pump, through the injector, through the column, and to the detector. There are strict requirements for the type and shape of tubing used for these connections. The tubing is typically a narrow bore capillary capable of withstanding very high pressures, up to 6000 psi or more. At the same time, the tubing needs to be flexible so as to provide easy manual hydraulic assembly of the different HPLC components. The fittings used for these connections should also be easy to assemble and at the same time be capable of withstanding significant pressure of the liquid. This is not easy to achieve and solutions are usually expensive and complicated. Multiple connections are required to be used to make up a continuous serial flow path.

Another problem involves the length of the tubing. It is advantageous for chromatography performance, especially efficiency of sample separation, to have the shortest and narrowest tubing possible connecting all the components of an HPLC system. When HPLC equipment is made up of spaced units, the length of all tubing cannot be shortened below a certain distance. Another issue with long narrow tubing is that it creates additional pressure resistance, which increases the need for greater pump pressure capacity. Another issue with multiple tubing and connectors is that they have a tendency to become plugged at connection points with components from the sample or with some other occasional particulate matter.

Another associated problem is temperature control of fluid and HPLC components. While traveling along long narrow tubing, liquid typically cools or warms to some equilibrium ambient temperature. In the case where elevated or a reduced temperatures are required for a particular analysis, each individual HPLC component needs to be thermally stabilized and liquid needs to be preheated or precooled every time it reaches an HPLC component, such as a detector or a column.

Still another problem of long narrow tubing is an ability of some chemicals to adsorb to the surface of the tubes, especially when the tubing is made of plastic, thereby producing a cross-contamination effect. It is a common problem especially in gradient chromatography elution mode. Typically, regular tube replacement is required to eliminate this phenomenon. Metal tubes are generally free of this effect, but they have their own limitations when used with certain chemicals. For example, they cannot be used with chloride solutions.

BRIEF SUMMARY OF THE INVENTION

The present invention is directed to overcoming one or more of the problems as set forth above.

The primary object of the present invention is to provide an integrated chromatography device that allows simple connection of an injector, a column, and a detector cell in one unit without any tubing interconnection.

The present invention is directed to providing a simple unified device having different HPLC elements or units that function together as a unit including a body having an inlet port and an outlet port and having affixed thereto or incorporated therein a plurality of typical HPLC elements, such as an injector, a column, and a detector.

It is a further object of the present invention to provide an integrated chromatography device that is inexpensive and can be easily manufactured by common machining or injection molding.

It is also an object of the invention to provide an integrated chromatography device that eliminates long tubing.

It is an additional object of the present invention to provide an integrated chromatography device that eliminates temperature difference among different HPLC units.

It is another object of the present invention to provide an integrated chromatography device that eliminates cross-contamination.

It is another object of the present invention to provide an integrated chromatography device that has very small dead volume resulting in high separation efficiency.

It is another object of the present invention to provide an integrated chromatography device that can hold high pressure without losing liquid connection.

It is another object of the present invention to provide an integrated chromatography device that by itself produces very little flow pressure resistance.

It is another object of the present invention to provide an integrated chromatography device that has no multiple connections and is essentially free of blockage.

It is still another object of the present invention to provide an integrated chromatography device that can be used with a variety solvents and mixtures.

In an exemplary embodiment of the present invention, an integrated chromatography device with several narrow internal flow passageways and several threaded ports provides a simple and efficient connection for all the above-mentioned HPLC components and forms a detector cell, an injector port and a column adapter.

BRIEF DESCRIPTION OF THE SEVERAL VIEWS OF THE DRAWINGS

The details of construction and operation of the invention are more fully described with reference to the accompanying drawings which form a part hereof and in which like reference numerals refer to like parts throughout.

In the drawings.

Figure 1:
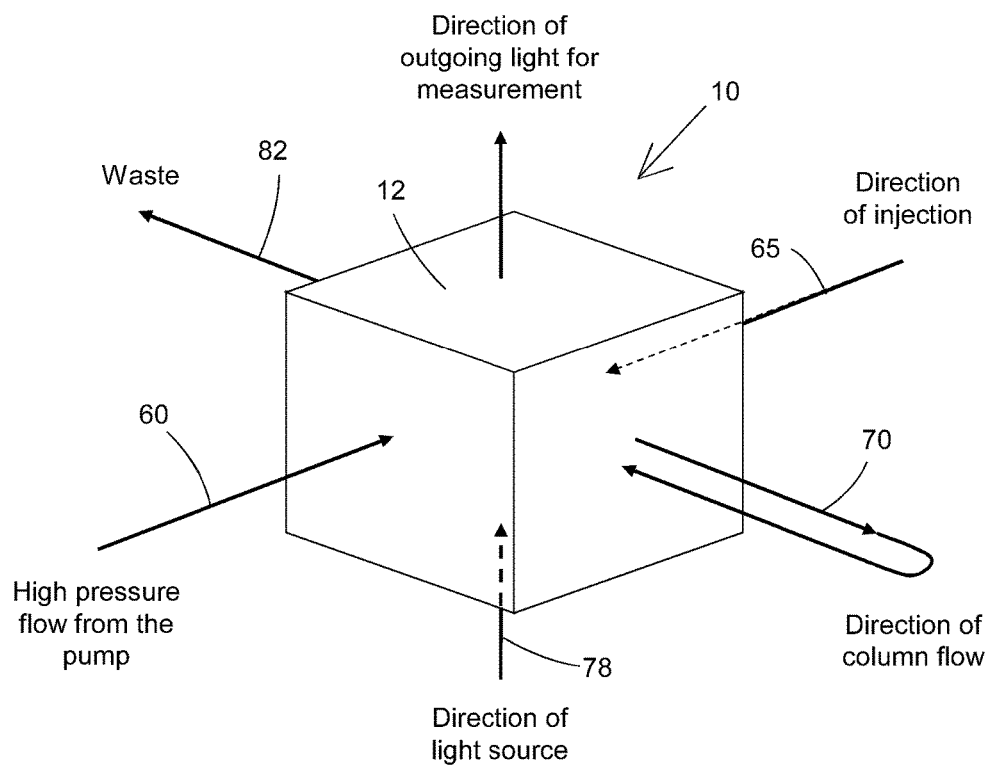
FIG. 1 is a general design schematic for an integrated chromatography device including a column, a detector cell, and an injector employing the concepts of the present invention.

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood.

DETAILED DESCRIPTION OF THE PREFERRED EMBODIMENTS

While the present invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated. This invention generally relates to high pressure liquid chromatography ("HPLC") and to ultra high pressure liquid chromatography ("UH-PLC"), but is not limited thereto and may by employed in other fields as well.

In FIG. 1, the main principal of integrated device, which combines a column, an injector and a detector, is presented and generally uses a three dimensional principal to arrange in a small volume all the components required for unification. Each component of the unification device is spaced along X, Y or Z space axes. For example, if the column is oriented along the "X" axis, then the injector cavity is oriented along the "Y" axis and the detector cell flow and detector light are oriented along the "Z" axis. This orientation allows the integrated device to be produced inexpensively by machining or injection molding with corresponding holes and threads to connect all the elements.

Figure 2:
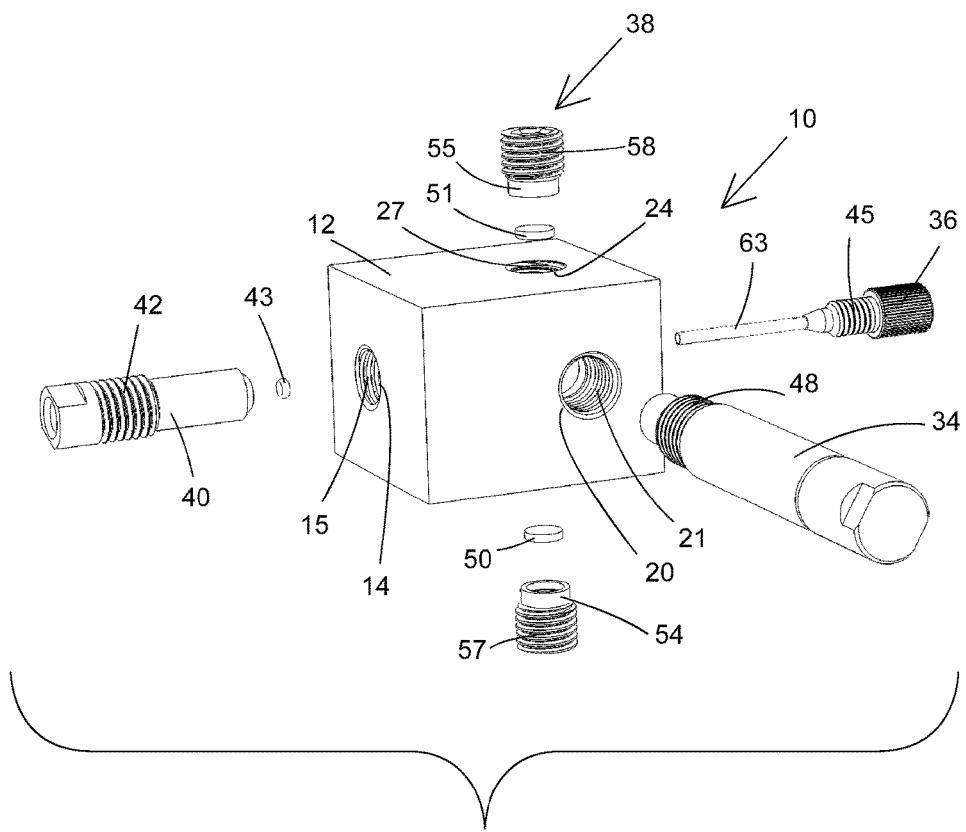
FIG. 2 is an exploded, perspective view of the integrated chromatography device employing the principles of the invention.
Figure 3:
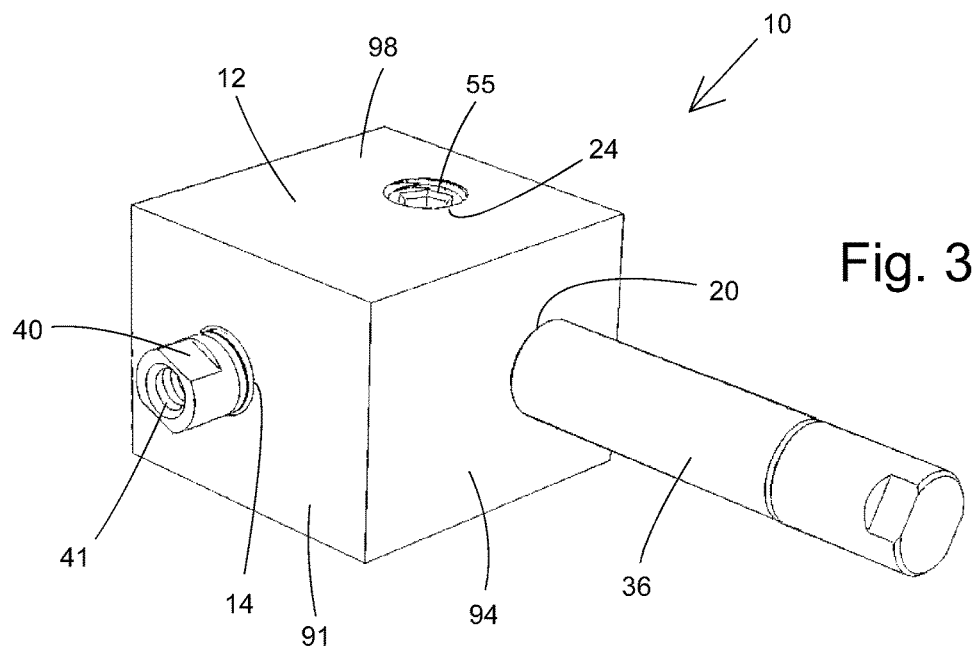
FIG. 3 is an external perspective view of the integrated chromatography device of FIG. 2 with components connected as seen from one corner.
Figure 4:
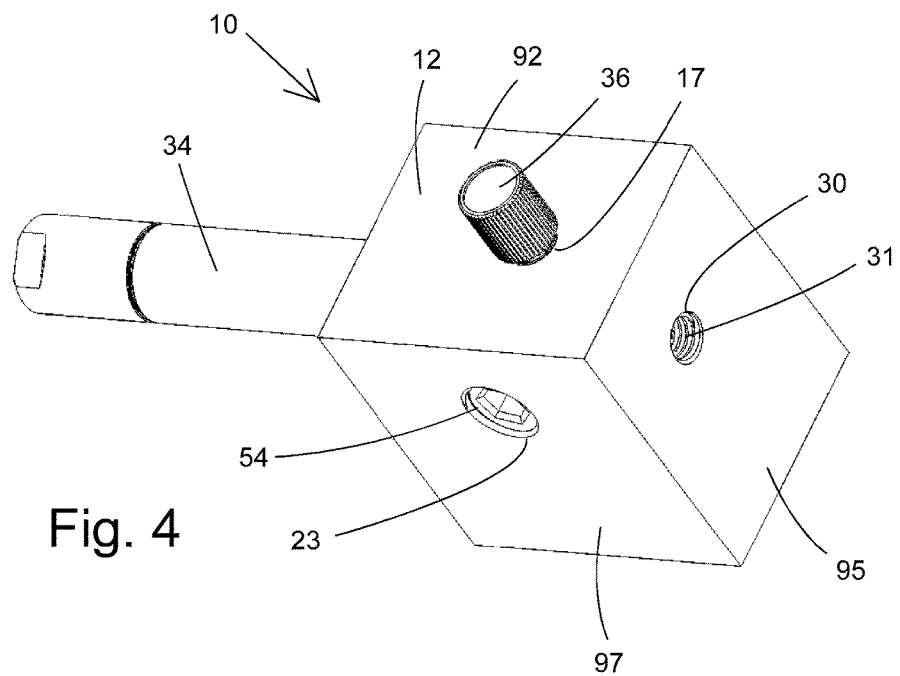
FIG. 4 is another external perspective view of the integrated chromatography device shown in FIG. 3 with components connected as seen from opposite corner; and, FIG. 5 is an exploded, perspective view of the integrated chromatography device shown in FIG. 2 with the body removed and the direction of fluid flow indicated.

As seen in FIGS. 2-4, an integrated HPLC device, generally designated 10, has an unitary main block body 12, or monobloc, including a body inlet port 14 with an internal thread 15, an injector connection port 17 with an internal thread (not shown), a column connection port 20 with an internal thread 21, a pair of opposed, optic mounting ports 23 and 24 with respective internal threads 27, and a body outlet port 30 with an internal thread 31. The body 12 is used to combine in one unit a removable column 34, a removable injector device 36, and a detector cell, generally designated 38. While the body 12 shown herein is a rectangular cuboid or block with rectangular side faces, it should be clear that other suitable shapes and configurations are possible without departing from the spirit of the invention.

The inlet port 14 and injector port 17 are arranged in spaced opposed relation along a longitudinal inlet-injector axis. The replaceable inlet port connector coupling 40 is tubular defining an internal connecting passageway 41, or through-bore, having an open outer end adapted for an external connection and an open inner end adapted to deliver fluid to downstream to the injector 36. The removable inlet coupling 40 has an external thread 42 adapted to engage the corresponding inlet port thread 15 so as to securely mount the coupling 40 to the body 12 as seen in FIGS. 2 and 3. An annular seal 43 is provided to make a fluid-tight connection between the inlet port connector coupling 40 and the injection stem 63 that is inserted into the connecting passageway 41 when the injector 36 is mounted within the connection port 17.

The introduction injector device 36 can be of the form disclosed in my co-pending United States Application entitled "Chromatography Sample Introduction Device" filed on Apr. 1, 2016, Ser. No. 15/089,461, which is incorporated herein by reference in its entirety. The injector device 36 has an external thread 45 adapted to engage the corresponding port thread so as mount the injector device 36 to the body 12 as seen in FIGS. 2 and 4 and effect a fluid-tight seal.

The column 34 has inlet and outlet ports (not shown) at the same end, which can be of the form as disclosed in my co-pending United States Application entitled "Chromatography Column with Inlet and Outlet at One End" filed on Apr. 1, 2016, Ser. No. 15/089,436, which is incorporated herein by reference in its entirety. The column 34 has an external thread 48 adapted to engage the corresponding port thread 21 so as to securely mount the column 34 to the body 12 along a longitudinal axis transverse to the inlet-injector axis as seen in FIGS. 2-5 and effect a fluid-tight seal.

The optical ports 23 and 24 are arranged in spaced opposed relation along a longitudinal optical axis transverse to the inlet-injector axis and the column axis. The ports 23 and 24 are each closed by optical windows 50 and 51 held sealingly in place by respective apertures or tubular socket set screws 54 and 55 having respective external threads 57 and 58 that engage respective body port threads 27. The construction of the optical detector may take the form as generally disclosed in my co-pending application Ser. No. 15/089,436, identified hereinabove. The optical windows 50 and 51 obstruct fluid flow from the internal optical flow path 75 to the exterior through the respective optical ports 23 and 24.

As seen in FIGS. 3 and 4, the body 12 is bounded by an external surface defined by the three pairs of opposed, spaced-apart faces. Axially aligned and spaced along a first axis are the body inlet port 14 and injector port 17 formed in parallel external faces 91 and 92, respectively. Axially aligned and spaced along a second axis orthogonal to the first axis are the column connection port 20 and the body outlet port 30 formed in parallel external faces 94 and 95, respectively. Axially aligned and spaced along a third axis orthogonal to the first and second axes are the detector ports, i.e., the optic mounting ports 23 and 24, formed in parallel external faces 97 and 98. While the external faces shown herein are rectangular, flat and in orthogonal relation and each only has a single port formed therein, other configurations are envisioned with similar functionality.

Figure 5:
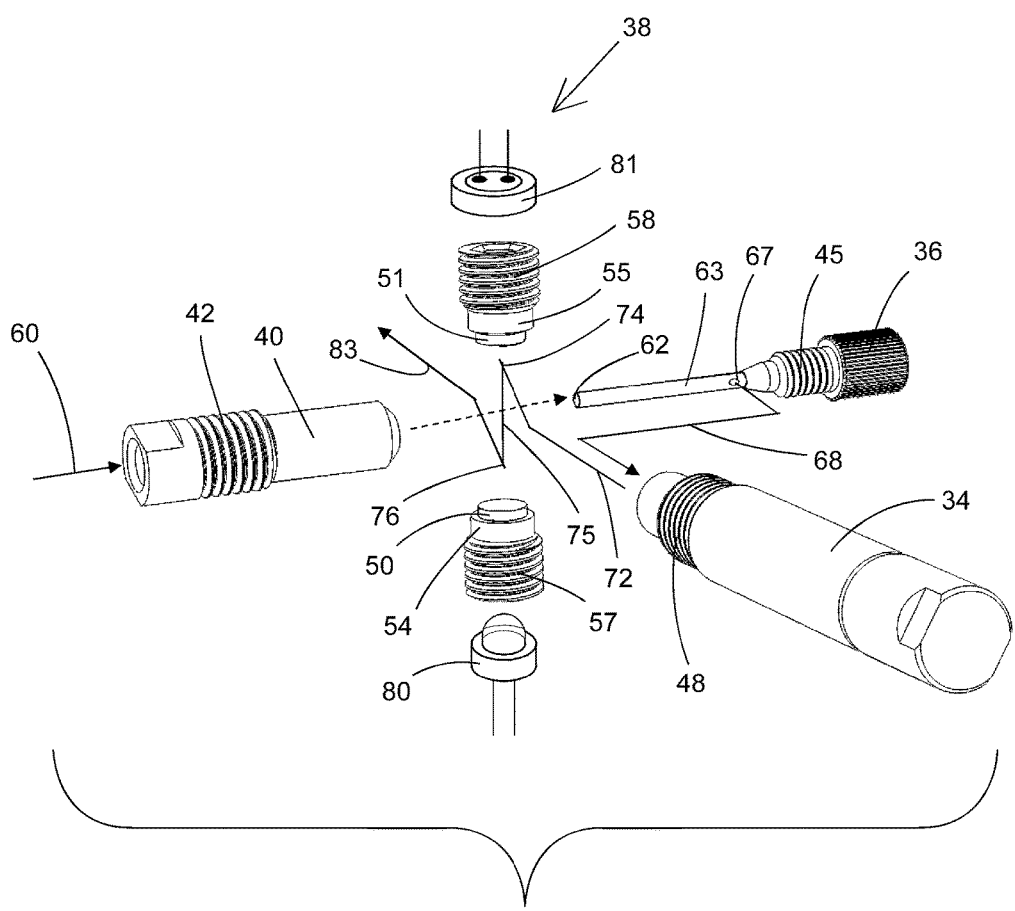

Short fluidic flow passageways are formed internally within the body 12 to enable fluid flow between the various connected component parts. As indicated in FIGS. 1 and 5, high pressure mobile phase fluid flows from a pump (not shown) and enters the upstream port 14 of the body 12 through the inlet coupling 40 as indicated by line 60. Thereafter, fluid exits the downstream end of the inlet coupling 40 and enters the upstream axial end 62 of the tubular injector stem 63 that has been inserted into the block body 12 as indicated by line 65. Fluid, now carrying a sample, exits the downstream radial outlet port 67 of the injector stem 63 and travels through a body flow passageway indicated by line 68 to the axial inlet port of the column 34 packed with stationary phase.

Thereafter, fluid loops through the column 34 as indicated by line 70 and then travels from the column outlet through a body flow passageway indicated by line 72 to the upstream end 74 of the optical flow path 75. Here, fluid is illuminated by a light beam 78 from external source 80 directed axially along the optical flow path 75 extending between the ports 23 and 24 toward the external detector 81, or other sensor, which collects light data for measurement. Fluid then exits the downstream end 76 of the optical flow path 75 through the body flow passageway indicated by line 83 and out the body outlet port 30 via a connecting coupling (not shown) as waste fluid.

INDUSTRIAL APPLICABILITY

It is understood that while the disclosed integrated column-injector-detector device is universal for many applications, modifications of this device can be made with different internal arrangements and with small deviations from exact X-Y-Z orientation to accommodate specific engineering goals.

It is also understood that the integrated column-injector-detector device can be made of several materials, such as inert plastic, stainless steel or other corrosion resistant metals, ceramic, etc.

It is also understood that the integrated column-injector-detector device can be of different sizes and the fluid passageways of differing diameter to accommodate the various requirements of the different chromatography types, such as preparative, analytical, or capillary.

It should be apparent the integrated column-injector-detector device described herein is a simple, functional unit that is effective and can be inexpensively mass manufactured.

An integrated column-injector-detector device constructed in accordance with the present invention provides a very simple and compact solution for unification of different chromatography components.

An integrated column-injector-detector device constructed in accordance with the present invention provides very little flow resistance because there are no long narrow passageways between components.

An integrated column-injector-detector device constructed in accordance with the present invention provides efficient chromatography because there is little internal dead volume.

An integrated column-injector-detector device constructed in accordance with the present invention provides minimized blocking by particulate matter because there are very few connections and long narrow tubing is not used.

An integrated column-injector-detector device constructed in accordance with the present invention provides even heat distribution among all the connected components if such control is required for a particular application. As disclosed in my co-pending application Ser. No. 15/089,436, identified hereinabove, a small heating element and controller can be employed with the device body to provide efficient thermal control.

An integrated column-injector-detector device constructed in accordance with the present invention limits contamination of the internal surfaces to very insignificant amounts because there is only very small surface area in contact with the fluid flow.

Other aspects, objects and advantages of this invention can be obtained from a study of the drawings and the foregoing disclosure.

It should be understood that the terms "first," "second," "inner," "outer," "inward," "outward," "end," "side," "length," and similar terms as used herein, have reference only to the structure shown in the drawings and are utilized only to facilitate describing the invention. The terms and expressions employed herein have been used as terms of description and not of limitation.

As used herein, the term "within" shall mean "to be partially or completely inside of"; the term "axial" refers to a direction that is substantially straight; the term "transverse" refers to a direction other than the axial direction (e.g., orthogonal or nonorthogonal); and, the term "fluid" refers to both liquids and gases.

From the foregoing, it will be observed that numerous variations and modifications may be effected without departing from the spirit and scope of the invention. It will also be observed that the various elements of the invention may be in any number of combinations, and that all of the combinations are not enumerated here. It will be understood that no limitation with respect to the specific apparatus illustrated herein is intended or should be inferred. While specific embodiments of the invention have been disclosed, one of ordinary skill in the art will recognize that one can modify the materials, dimensions and particulars of the embodiments without straying from the inventive concept.

What is claimed is:

1. A chromatography device comprising:
   a body bounded by an external surface and having upstream inlet and downstream outlet ports, first and second connection ports, and at least one detector port, said ports extending inwardly from said external surface;
   a connector coupling removably mounted in the inlet port defining an internal connecting passageway extending axially between inner and outer ends, the outer end being adapted to receive an external connection;
   a sample injector removably mounted in the first connection port, the sample injector having a tubular stem for carrying sample to be analyzed with an upstream inlet at one end and a downstream outlet spaced from said one end, said stem extending into the inner end of the connecting passageway when said injector is mounted;
   a chromatography column having one end removably mounted in the second connection port and having at said column one end an upstream inlet and a downstream outlet located in the second connection port when the column is mounted;
   a detector for chromatography measurement located at the detector port;
   said body defining a first internal flow passageway between the first connection port and the second connection port providing fluid communication between the downstream outlet of a sample injector mounted in the first connection port and the upstream inlet of a chromatography column mounted in the second connection port;
   said body defining a second internal flow passageway between the second connection port and the outlet port providing fluid communication between the downstream outlet of a chromatography column mounted in the second connection port and a segment of the second internal flow passageway extending past the detector; and, whereby fluid enters the input port of said body and exits the output port of said body.

2. The chromatography device of claim 1 wherein said body is a unitary monobloc.

3. The chromatography device of claim 1 wherein said body has two detector ports axially aligned, one detector port being formed in one side of said external surface and the other detector port being formed in a side of said external surface spaced from and opposing said one side.

4. The chromatography device of claim 3 further including an optical window mounted in each of said two detector ports, each optical window obstructing fluid flow from said second internal passageway through its respective detector port from an internal side of the optical window to an external side of the optical window.

5. The chromatography device of claim 4 wherein said detector is located on the external side of one optical window and a light source is located on the external side of the other optical window.

6. The chromatography device of claim 5 wherein said second internal passageway includes an optical flow path extending axially between said optical windows intermediate upstream and downstream portions of the second internal passageway.

7. The chromatography device of claim 1 wherein the inlet port has an internal thread and said connector coupling has an external thread adapted to engage said internal thread of the inlet port to secure said connector coupling in the inlet port when mounted therein.

8. The chromatography device of claim 1 wherein the injector port has an internal thread and said injector has a tubular stem at one end that extends into the connecting passageway, a gripping portion at the other end, and an intermediate external thread adapted to engage said internal thread of the injector port to secure said injector in the injector port when mounted therein.

9. The chromatography device of claim 1 wherein the second connection port has an internal thread and said chromatography column has an external thread adapted to engage said internal thread of the second connection port to secure said chromatography column in the second connection port when mounted therein.

10. The chromatography device of claim 1 wherein said body is made of one of stainless steel, corrosion-resistant metal, inert plastic, and ceramic.

11. The chromatography device of claim 1 wherein said external surface includes a first pair of external faces spaced along and orthogonal to a first axis, a second pair of external faces spaced along and orthogonal to a second axis orthogonal to said first axis, and a third pair of external faces spaced along and orthogonal to a third axis orthogonal to said first and second axes, and wherein each of said ports is formed in and orthogonal to one of said external faces.

12. A chromatography device comprising:
a body bounded by an external surface and having upstream inlet and downstream outlet ports, first and second connection ports, and at least one detector port, said ports extending inwardly from said external surface;
a sample injector for carrying sample to be analyzed removably mounted in the first connection port and having an upstream inlet and a downstream outlet, said injector inlet communicating with the body inlet port through a connecting passageway;
a chromatography column having one end removably mounted in the second connection port and having at said column one end an upstream inlet and a downstream outlet located in the second connection port when the column is mounted;
a detector for chromatography measurement located at the detector port; and,
said body defining a first internal flow passageway between the first connection port and the second connection port providing fluid communication between the downstream outlet of a sample injector mounted in the first connection port and the upstream inlet of a chromatography column mounted in the second connection port;
said body defining a second internal flow passageway between the second connection port and the outlet port providing fluid communication between the downstream outlet of a chromatography column mounted in the second connection port and a segment of the second internal flow passageway extending past the detector; and,
whereby fluid enters the input port of said body and exits the output port of said body.

13. The chromatography device of claim 12 wherein said body is a unitary monobloc.

14. The chromatography device of claim 12 wherein the inlet port and the first connection port are axially aligned, the inlet port being formed in one side of said external surface and the first connection port being formed in a side of said external surface spaced from and opposing said one side.

15. The chromatography device of claim 14 further including a removable connector coupling mounted within the inlet port defining said connecting passageway extending axially between inner and outer ends, the outer end being adapted to receive an external connection.

16. The chromatography device of claim 15 wherein said injector has a tubular stem at one end that extends into the connecting passageway and a gripping portion at the other end, the inlet of said injector is located at the extending end of the stem and the outlet of said injector is located intermediate said injector ends, and said stem extends into the inner end of the connecting passageway when said injector is mounted.

17. The chromatography device of claim 12 wherein said body has two detector ports axially aligned, one detector port being formed in one side of said external surface and the other detector port being formed in a side of said external surface spaced from and opposing said one side, and further including an optical window mounted in each of said two detector ports obstructing fluid flow from said second internal passageway through its respective detector port from an internal side of the optical window to an external side of the optical window, and wherein said detector is located on the external side of one optical window and a light source is located on the external side of the other optical window.

18. A chromatography device comprising:
a solid body bounded by an external surface and having upstream inlet and downstream outlet ports, first and second connection ports, and at least one detector port, said ports extending inwardly from said external surface;
a connector coupling removably mounted in the inlet port defining an internal connecting passageway extending axially between inner and outer ends, the outer end being adapted to receive an external connection, the connector coupling having an external thread for cooperatively engaging an internal thread formed in the input port to secure the connector coupling thereto;

a sample injector removably mounted in the first connection port, and the sample injector having a tubular stem for carrying sample to be analyzed with an upstream inlet at one end and a downstream outlet spaced from said one end, said stem extending into the inner end of the connecting passageway when said injector is mounted, the sample injector having an external thread for cooperatively engaging an internal thread formed in the first connection port to secure the sample injector thereto;

a chromatography column having one end removably mounted in the second connection port and having at said column one end an upstream inlet and a downstream outlet located in the second connection port when said column is mounted, the chromatography column having an external thread for cooperatively engaging an internal thread formed in the second connection port to secure the chromatography column thereto;

a detector for chromatography measurement located at the detector port;

said body defining a first internal flow passageway between the first connection port and the second connection port providing fluid communication between the downstream outlet of a sample injector mounted in the first connection port and the upstream inlet of a chromatography column mounted in the second connection port;

said body defining a second internal flow passageway between the second connection port and the outlet port providing fluid communication between the downstream outlet of a chromatography column mounted in the second connection port and a segment of the second internal flow passageway extending past the detector; and, whereby fluid enters the input port of said body and exits the output port of said body.

* * * * *